US008647332B2

(12) United States Patent
Bernabei

(10) Patent No.: US 8,647,332 B2
(45) Date of Patent: Feb. 11, 2014

(54) METHOD AND APPARATUS FOR QUASI-FRACTIONAL INTENSE PULSE LIGHT RESURFACING

(75) Inventor: Gian Franco Bernabei, Florence (IT)

(73) Assignee: Mattioli Engineering Ltd., London (GB)

( * ) Notice: Subject to any disclaimer, the term of this patent is extended or adjusted under 35 U.S.C. 154(b) by 1097 days.

(21) Appl. No.: 12/606,954

(22) Filed: Oct. 27, 2009

(65) Prior Publication Data

US 2010/0174277 A1 Jul. 8, 2010

Related U.S. Application Data

(63) Continuation-in-part of application No. 12/350,466, filed on Jan. 8, 2009.

(51) Int. Cl.
*A61B 18/18* (2006.01)
(52) U.S. Cl.
USPC .................................. 606/2; 606/41; 607/88
(58) Field of Classification Search
USPC .................................. 606/2–19; 607/88–94
See application file for complete search history.

(56) References Cited

U.S. PATENT DOCUMENTS

| | | | |
|---|---|---|---|
| 3,610,741 A | 10/1971 | Davies et al. | |
| 6,269,271 B1 | 7/2001 | Bernabei | |
| 6,518,538 B2 | 2/2003 | Bernabei | |
| 6,702,808 B1 | 3/2004 | Kreindel | |
| 2005/0199900 A1 | 9/2005 | Lin et al. | |
| 2006/0155266 A1* | 7/2006 | Manstein et al. | 606/17 |
| 2006/0189964 A1* | 8/2006 | Anderson et al. | 606/9 |
| 2006/0271028 A1* | 11/2006 | Altshuler et al. | 606/9 |
| 2008/0021442 A1 | 1/2008 | Manstein et al. | |
| 2009/0054957 A1* | 2/2009 | Shanbaky | 607/89 |

FOREIGN PATENT DOCUMENTS

IT 01286634 5/1996

OTHER PUBLICATIONS

Office Action cited in related U.S. Appl. No. 12/350,466, dated Jun. 6, 2012.

* cited by examiner

*Primary Examiner* — Aaron Roane
(74) *Attorney, Agent, or Firm* — Phillip J. Articola; MOTS Law, PLLC

(57) ABSTRACT

A system and method for treating a skin target area includes one or more RF electrodes adapted to provide RF energy for heating the skin target area. A quasi-fractional light unit is adapted to provide optical spots of energy having a wavelength not greater than 1200 nm for heating the skin target area. The RF electrodes and the quasi-fractional light unit are configured to provide energy essentially simultaneously to the skin target area to heat the entire target in non-uniform manner by way of a matrix of spots each having a predetermined diameter.

9 Claims, 5 Drawing Sheets

*FILETTATURA M3*

METHOD AND APPARATUS FOR QUASI-FRACTIONAL INTENSE PULSE LIGHT RESURFACING

RELATED APPLICATIONS

This application is a Continuation-In-Part of U.S. patent application Ser. No. 12/350,466, filed on Jan. 8, 2009, the disclosure of which is incorporated in its entirety into this application herein by reference.

BACKGROUND OF THE INVENTION

1. Field of the Invention

The present invention relates to a method and apparatus for applying to the skin, in a controlled manner, light to the skin in order to heat and selectively damage thin superficial layers of the skin, thereby inducing a renewal process of the epidermis.

2. Description of the Related Art

It is well known in the skin treatment art that in order to renew the epidermis layer, induced damage of the skin is required. One such method uses laser radiation that is incident on the skin and that generates several effects on the skin, depending on the wavelength of the laser radiation, the pulse duration of the laser energy applied to the skin, and the radiation energy provided to the skin.

The most commonly used method is $CO_2$ laser radiation for generating a superficial heating of the skin. When laser light reaches the skin, its intensity decreases exponentially as it progresses down into lower layers of the skin. This means that the thermal energy that is delivered is higher in the first layer and decreases exponentially as its progresses down to lower layers of the skin. Moreover, the first corneum stratus of the skin has a higher absorption than other layers. Such an energy profile is not suitable for a uniform heating of a volume of skin due to the fact that in the superficial (upper) layers, the reached temperature is too high and in the lower layers the reached temperature is not high enough to trigger the desired skin treatment process.

Another method is to increase the temperature of the skin by heating through radiofrequency. In U.S. Pat. No. 6,269,271, which is incorporated in its entirety herein by reference, radio frequency current pulses are applied to the skin in a controlled manner in order to heat selected volumes of skin, thereby inducing the removal of unwanted pigments from the skin. A probe provides the radio frequency current pulses to the skin, where the probe includes first and second metallic stripes, and where the probe is connected to two coaxial cables that are respectively connected to the first and second metallic stripes. The two coaxial cables are connected to a balanced/unbalanced transformer, which in turn is connected to a radio frequency generator that provides radio frequency pulses.

Two principles are used in U.S. Pat. No. 6,518,538, which is incorporated in its entirety herein by reference. First, radio frequency currents are localized in the external layer of the skin due to the skin effect, and thus the heating is localized in a thin (upper) layer of skin.

It is well known that an alternating voltage applied to a conductor generates a current on the external layer of the conductor and the depth depends on the frequency and the resistance of the conductor (so-called skin effect).

Second, the plasma generated at the contact of the skin, due to the radio frequency and a high vacuum generated by a suitable pump, is composed of high energy gas ions that strike the surface of the skin, thereby generating heat in the superficial layer of the skin.

The interaction with the skin has some similarities to the interaction described in U.S. Pat. No. 6,269,271, which is incorporated in its entirety herein by reference.

One advantage of such an approach is by not having electrodes in contact with the skin, a more even distribution of the radio frequency current in the skin is achieved. Also, there is achieved a combined action from the striking gas ions and a more accurate control of the power applied to the skin surface, due to the higher impedance of the plasma that controls the current independently from the electrical conductivity value of the skin.

U.S. Pat. No. 6,518,538 describes an apparatus and a method for skin resurfacing treatment, which provides induced thermal damage of the skin by radio frequency heating and by ion bombardment of the skin.

In U.S. Pat. No. 6,518,538, this dual effect may be achieved by using a pulsed radio frequency generator connected to a probe for coupling to the skin. The probe is preferably made of a non-conductive material (such as glass or plastic), and enables the application of a high vacuum to the skin surface (e.g., 5-10 millibars) over a predetermined (e.g., round) portion of the skin, by using a non-conductive pipe connected to a vacuum pump. At a suitable distance (around 10 millimeters) from the surface of the skin, an electrode (that is housed within the probe) is used to generate a radio frequency field between the electrode itself and the surface of the skin. After reaching a sufficient vacuum (e.g., 5-10 millibars of atmospheric pressure), a high voltage radio frequency electric field is applied between the electrode and the surface of the skin, due to a radio frequency pulse applied to the electrode. Such a radio frequency field triggers a glow discharge inside the probe between the electrode and the skin. A radio frequency current, due to the low impedance of the glow discharge, flows evenly on the surface of the skin, and, due to the skin effect, is limited to the glow discharge area in a depth of about 300 microns. In the surrounding tissues, the current density decreases by the square of the distance from the area covered by the glow discharge within a depth of 300 microns. Moreover, the high energy ions of the glow discharge strike the surface of the skin, thereby providing a plasma skin resurfacing that can be used to remove spider veins, skin brown spots, or port wine stains, for example.

U.S. Pat. No. 6,518,538 describes the providing of a controlled heating of a selected portion of the skin to a depth of about 300 microns. As a result, it is possible to reach a desired temperature of 70 degrees C. or more, which triggers controlled damage to the skin cells to achieve a desired effect. The temperature reached in the described volume of the skin depends primarily on the selected pulse length and the power of the radio frequency generator. Preferably, a temperature reached in the described volume of the skin is a temperature in the range of from 75 degrees C. to 95 degrees C.

U.S. Patent Publication No. 20080021442, which is incorporated in its entirety herein by reference, describes a method and apparatus that use optical radiation to ablate or damage a target area of skin surface for dermatological treatment, which skin surface includes the epidermis and parts of the dermis as the objective or side effect of the desired treatment. In U.S. Patent Publication No. 20080021442, delivery of the electromagnetic radiation to the skin in a predetermined pattern is achieved by either masking parts of the target area of the skin surface in order to protect the masked parts of the skin surface from the electromagnetic radiation, or by utilizing a light beam of relatively small diameter which is scanned across the skin surface by various means in order to generate a specific pattern for affecting superficial thermal skin injury.

The parts of the target area of the skin surface are masked by providing a mask between a light source and the patient's skin, whereby the mask includes many small holes for allowing light to pass from the light source to the patient's skin, and whereby all other portions of the mask that do not have holes entirely block the light from passing through the mask to the patient's skin.

SUMMARY OF THE INVENTION

One aspect of the present invention is directed to a system for treating a skin target area. The system includes one or more RF electrodes adapted to provide RF energy for heating the skin target area. The system also includes a quasi-fractional light unit adapted to provide optical spots of energy having a wavelength not greater than 1200 nm for heating the skin target area, the RF electrodes and the quasi-fractional light unit being configured to provide energy essentially simultaneously to the skin target area to heat the entire target in non uniform way by way of a matrix of small spaced spots of 500 micron diameter spaced 150 micron apart from adjacently-positioned spots.

Another aspect of the present invention is directed to a method for treating a skin target area. The method includes providing, by way of one or more RF electrodes, RF energy for heating the skin target area. The method also includes providing, by a quasi-fractional light unit, optical spots of energy having a wavelength not greater than 1200 nm for heating the skin target area, the RF electrodes. The energy provided by the quasi-fractional light unit is provided energy essentially simultaneously to the skin target area to heat the entire target in non uniform way by way of a matrix of small spaced spots of 500 micron diameter spaced 150 micron apart. The method can be performed in part by using computer software code stored in computer readable medium (e.g., a computer disk), whereby the computer software code provides control of a laser light source.

A non-transparent shield with a matrix of holes can be provided adjacent a light source to provide the matrix of small spaced spots of light to be incident on an area of skin to be treated. One advantage using a non-transparent shield is to provide a uniform increase of the temperature on the treated area and a higher increase of the temperature where the holes are located. Instead, in the non-transparent shield solution, the increase in the temperature occurs only in the holes. This avoids the delivery of too high energy in the holes for heating the skin and thus limiting the possible damages to the skin that occurs when the energy per square centimeter is too high, i.e. more than 30 Joule/square centimeters. One material that has been found suitable for use in a shield for this application is Aluminum Oxide, with holes laser drilled in the shield. The research of the suitable material has been extremely complex. There is the need to avoid increase of the temperature of the shield during the application, but at the same time provide a sufficient amount (e.g., 75%) of attenuation. The Aluminum Oxide shield reflects 70% of the radiation and transmit the radiation with small attenuation around 5%, thus avoiding increase of the temperature of the shield.

BRIEF DESCRIPTION OF THE DRAWINGS

The invention will become more fully apparent from the following detailed description when read in conjunction with the accompanying drawings with like reference numerals indicating corresponding parts throughout, and wherein.

DETAILED DESCRIPTION OF THE PREFERRED EMBODIMENTS

Preferred embodiments of the present invention will be described in detail hereinbelow, with reference to the drawings.

According to the present invention, a skin treatment device is put in contact or adjacent to a patient's skin to be treated, whereby a semi-transparent shield, or mask, is also provided as the distal end of the probe closest to the skin when the skin is treated by the probe. The shield operates to limit the amount of electromagnetic radiation, so as to limit the amount of any damage that may occur to the skin and to apply the electromagnetic radiation with a specific pattern.

Figure 1:
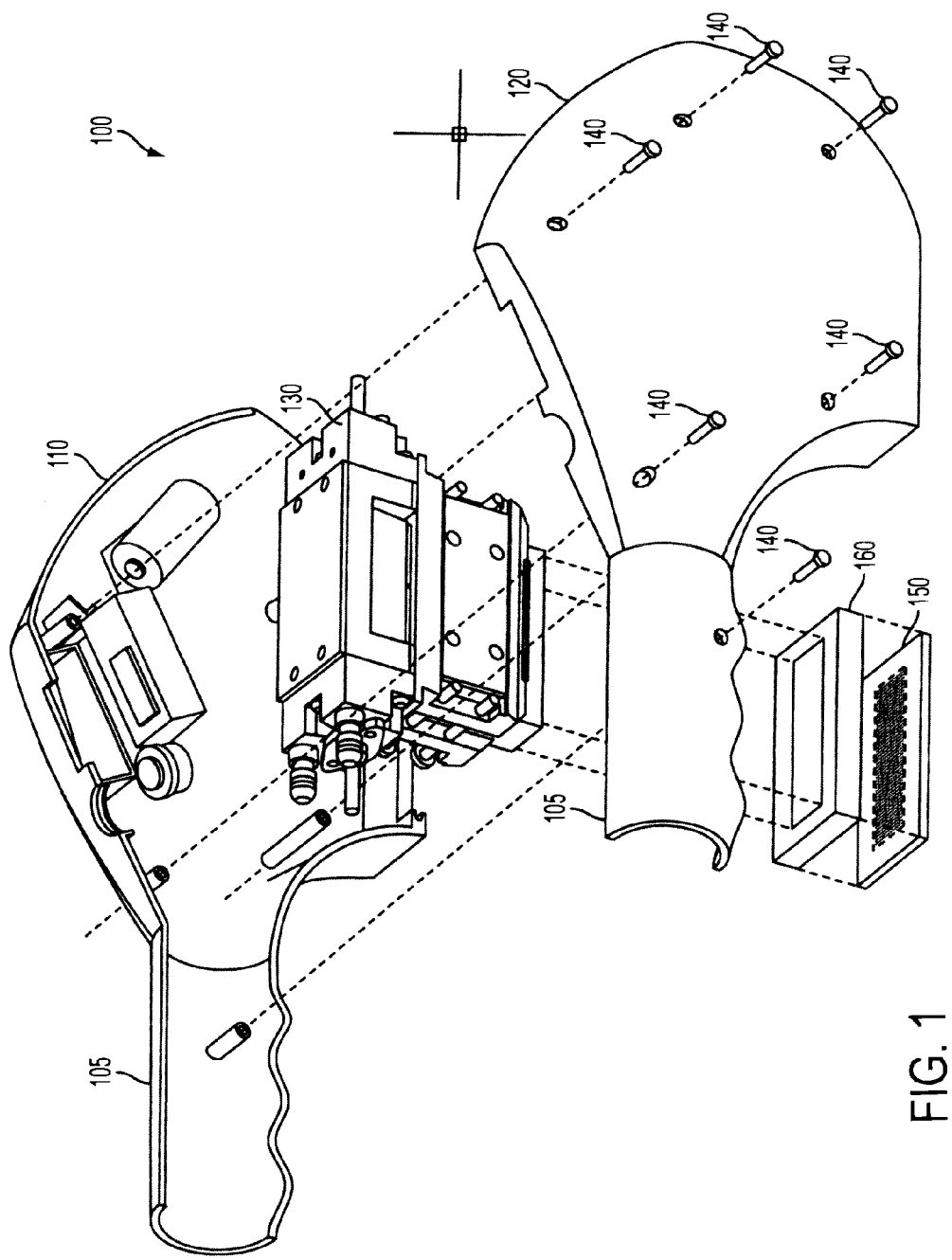
FIG. 1 shows a device that may be utilized to treat a skin surface in order to provide skin heating, in accordance with a first embodiment of the invention.

FIG. 1 is a view of the various components making up a skin treatment device 100 according to a first embodiment of the invention. The skin treatment device includes a left-side housing 110 and a right-side housing 120, and a light source 130 disposed within the housings 110, 120. The left and right-side housings 110, 120 are preferably attached to each other, with the light source 130 fixed therebetween, by a plurality of screws 140. A grip portion 105 is provided on the left and right-side housings 110, 120, so that an operator can firmly grasp the skin treatment device 100 so as to treat a particular region of a patient's skin. In the first embodiment, the light source 130 is a Xe lamp light source, which outputs light at an intensity of 150 Joules. Other types of laser light sources may be utilized, while remaining within the spirit and scope of the invention.

At the bottom of the light source 130, through which light is output towards a patient's skin, a shield 150 and shield holding unit 160 are connected.

Figure 2A:
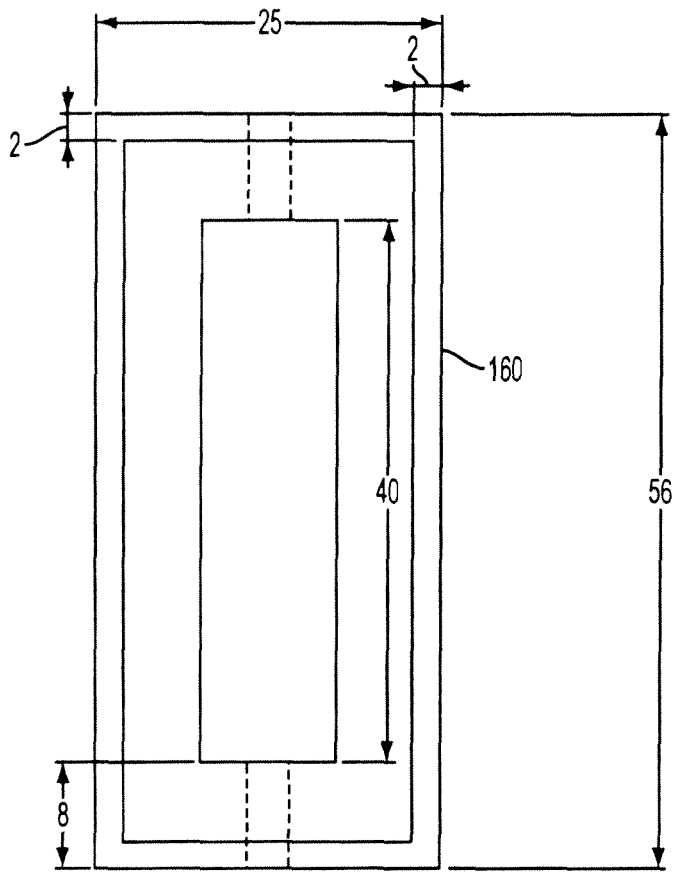
FIGS. 2A, 2B and 2C show different view angles of a shield holding unit in accordance with the first embodiment of the invention.
Figure 2B:
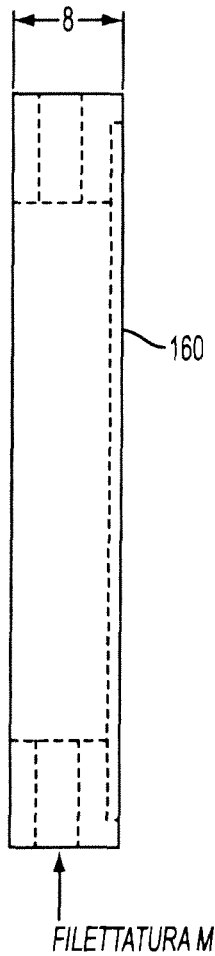
Figure 2C:
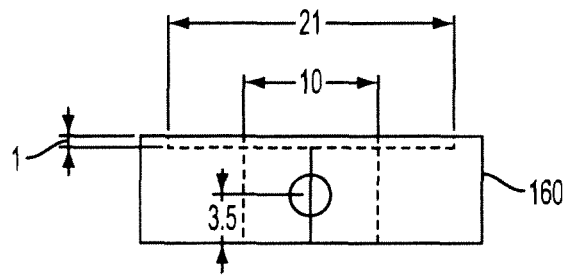

Turning now to FIGS. 2A, 2B and 2C, the shield holding unit 160 is sized to have fitted therein the shield 150, whereby FIG. 2A is a top-down view of the shield holding unit 160, FIG. 2B is a side view of the shield holding unit 160, and FIG. 2C is a front view of the shield holding unit 160. The shield holding unit 160 may be 25 mm by 56 mm in size, with a 21 mm×52 mm opening to thereby fit the shield 150 within the shield holding unit 160.

Figures 3A, 3B:
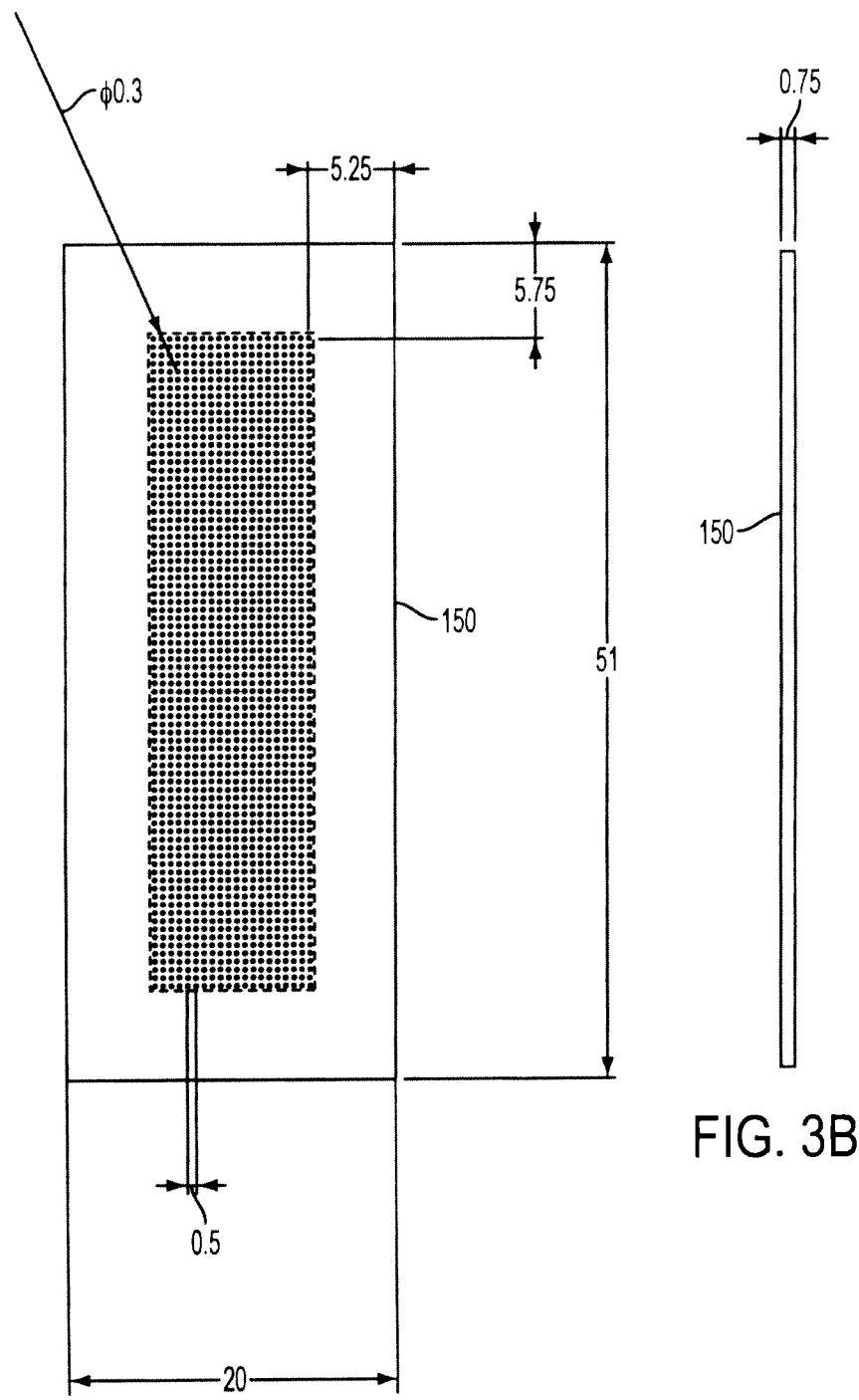
FIGS. 3A and 3B show different view angles of a shield in accordance with the first embodiment of the invention.

FIG. 3A is a top-down view of the shield 150, and FIG. 3B is a side view of the shield 150. The shield 150 includes a plurality of holes that are provided in a matrix pattern, whereby the holes are 0.5 mm apart from each other in one possible implementation of the shield 150. Other hole spacings are possible while remaining within the spirit and scope of the invention. The shield 150 is sized to fit within the opening of the shield holding unit 160, so that it is held firmly in place within that opening. By way of example, for the 21 mm×52 mm opening of the shield holding unit 160 shown in FIGS. 2A, 2B and 2C, a shield 150 having a 20 mm×51 mm size, such as shown in FIGS. 3A and 3B, is snugly fitted within that opening.

Each of the holes of the shield 150 pass entirely through the shield 150, so as to allow light from the light source 130 to contact the skin of a patient in a non-attenuated manner.

In the first embodiment, the shield 150 is made of a ceramic material, so that the non-hole portions of the shield 150 allow light from the light source 130 to pass through those portions of the shield 150 in an attenuated manner. In one possible implementation, light from the light source 130 passes through the non-hole portions of the shield 150 at 75% of their output light power, thereby resulting in a 25% attenuation due to the ceramic material making up the shield 150 being in the light path to the patient's skin. Other attenuation amounts, such as 15% to 35%, may be utilized while remaining within the spirit and scope of the invention.

By controlling the light amount to be incident on the patient's skin by way of the holes of the shield 150 and by controlling the total amount of light to be incident on the patient's skin by using a shield 150 made of a ceramic material, all portions of the patient's skin are subject to at least some amount of light (and thus are treated), whereby the patient is not subject to too much light output so as to cause damage to the patient's skin. The attenuation amount of the light output from the light source 130 to the patient's skin can be changed by using a thicker or thinner ceramic shield 150, as desired, by easily removing one shield from the shield holding unit 160 and placing another shield into the shield holding unit 160.

In one possible implementation, the ceramic shield 150 according to the first embodiment is made up of the following material: Aluminum Oxide. In another possible implementation, the ceramic shield is constructed from transparent plastic (e.g., polycarbonate), with an optical reflective coating provide thereon, and whereby the holes are provided on the plastic shield by an injection molding process. The optical reflective coating is 75% reflective, and the plastic is 100% transparent, thereby providing a shield having 25% attenuation of light in non-hole portions of the shield (the hole portions of the shield pass through light unattenuated). Of course, to achieve other amounts of attenuation, the optical reflective coating is manufactured to have a particular reflective value (e.g., 70% reflectivity to thereby provide a shield having 30% attenuation of light in non-hole portions of the shield; 80% reflectivity to thereby provide a shield having 20% attenuation of light in non-hole portions of the shield). By utilizing a device according to the first embodiment, hot spots are generated on the epidermis at a temperature of between 65-70° C., surrounded by tissue heated at approximately 50° C. This is due to the use of the fractional pulse light and tissue in the dermis heated in a uniform way at approximately 45° C. by usage of radiofrequency pulses. One possible sequence that can be used is outputting a radiofrequency for one second that heats up the dermis and the epidermis at 45° C., and in the last 15 milliseconds of the radiofrequency output, generating two pulses of fractional light that create the hot spots at 65-70° C. surrounded by tissue heated at 50° C. After the two pulses are output, the epidermis is allowed to decrease in temperature to approximately 36° C.

In a second embodiment, the light source 130 is a $CO_2$ laser operated in a fractional mode, i.e., with a matrix of dots, as described in Italian Patent No. 01286634 (F1196A118). The $CO_2$ laser is used to output a single large diameter light beam (non-fractional mode), whereby the combination of the $CO_2$ laser and the shield provides for a single light beam with a large diameter, which is similar to the output light pattern obtained by using a small diameter laser beam and a wobbling mirror as described in Italian Patent No. 01286634 (F1196A118).

In the first and second embodiments, the use of fractional light generates localized "injuries" on the skin, in order that the spots of injured skin are surrounded by healthy tissue (whereby the healthy tissue is heated a little in order to stimulate regrowth). This is accomplished by creating hot spots where the temperature is well over the damaging temperature value of the epidermis cell, whereby the hot spots are surrounded by areas where the skin temperature is higher than 36 degrees C. but significantly less than the damaging temperature value of the epidermis cell (and thus significantly less than the hot spots). The damaging temperature value of the epidermis cell is approximately 65 degrees C. The areas surrounding the hot spots are skin areas in which light has passed through the solid portion of the shield (e.g., not through the holes of the shield) and then onto the respective skin areas. In this way, the healthy skin tissue surrounding the hot spots on the skin will help the recovery of the damaged skin tissue and allow for faster regrowth to occur, so as to reduce wrinkles on the skin, for example.

Figure 4:
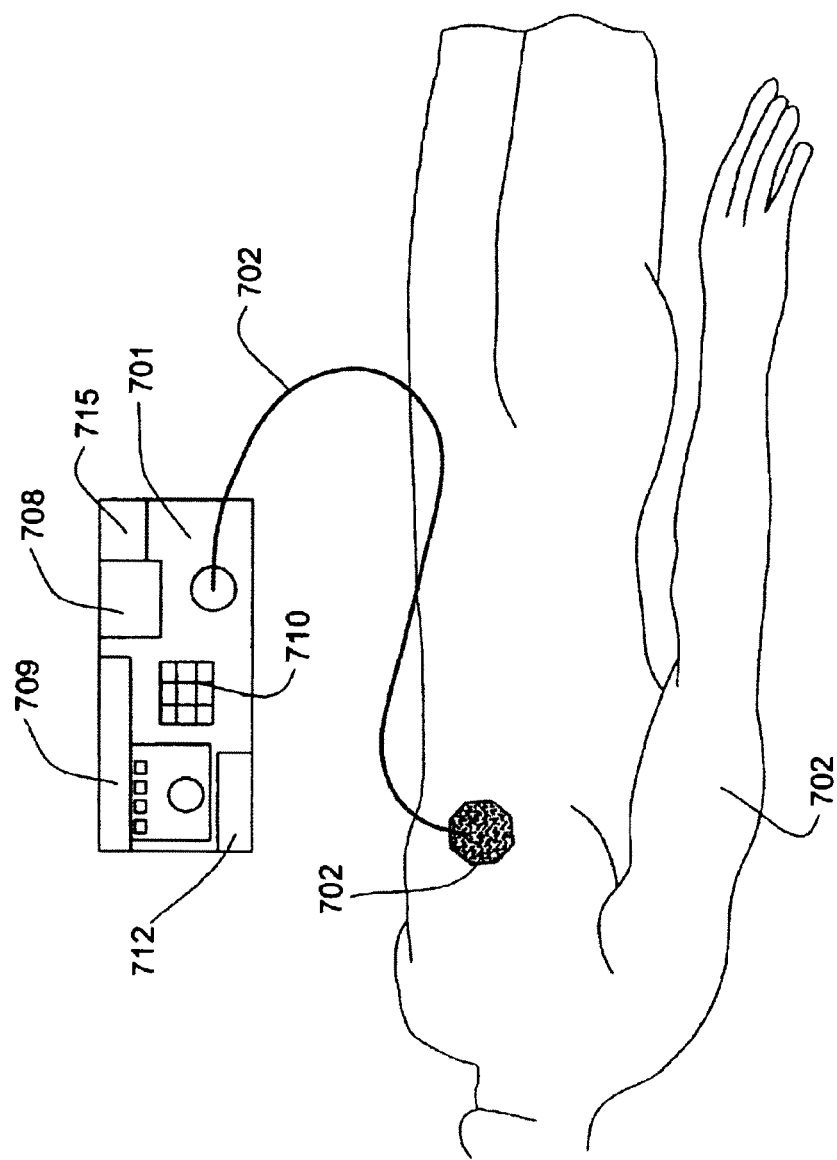
FIG. 4 shows a system for simultaneously applying RF and optical energy to an individual in accordance with a third embodiment of the invention.
Figure 5:
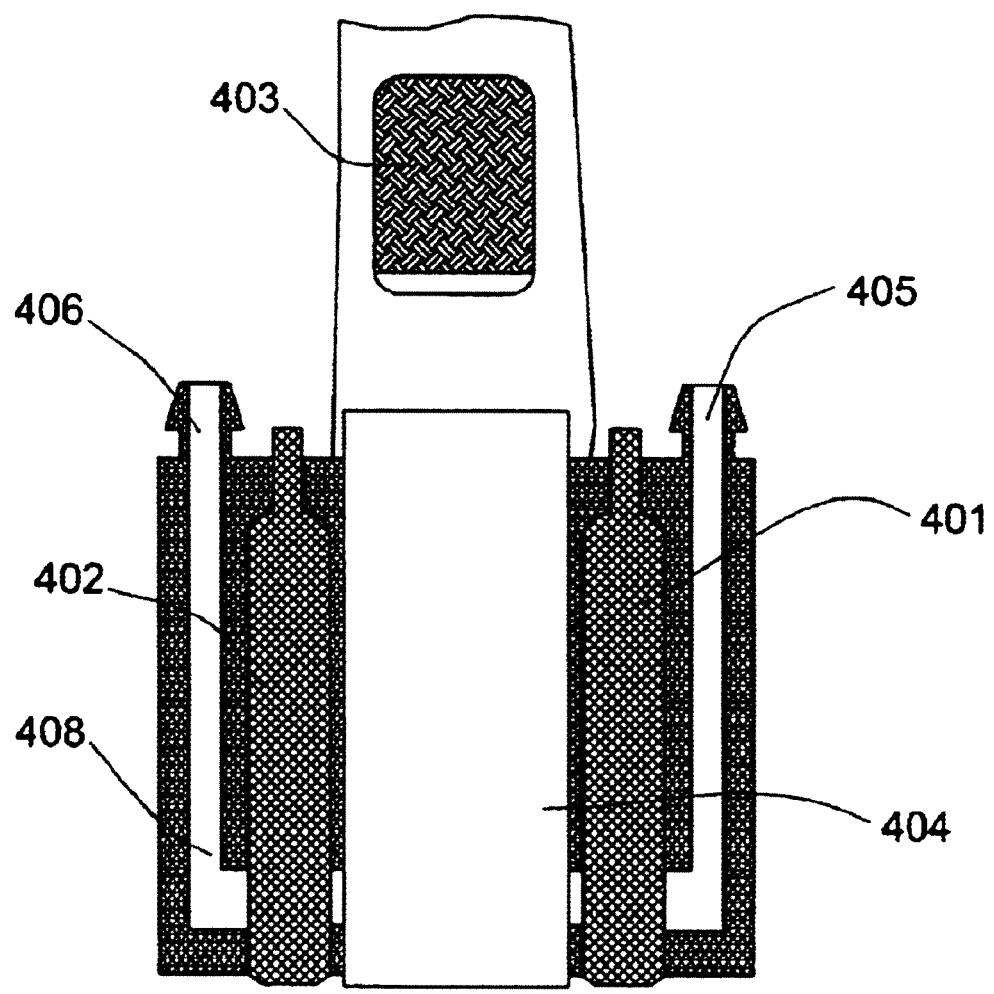
FIG. 5 shows an applicator with two electrodes, light source and cooling system in accordance with a third embodiment of the invention.

A third embodiment of the invention is described hereinbelow, which includes a quasi-fractional intense pulse light resurfacing device as described above. The third embodiment described below is based on a device described in U.S. Pat. No. 6,702,808 (the '808 patent', the disclosure of which is incorporated in its entirety herein by reference), but which uses quasi-fractional light instead of using non-fractional light provided by a standard light source. FIGS. 4 and 5, described below, correspond to FIGS. 3 and 4 of the '808 patent, but whereby quasi-fractional intense pulse light is used in the third embodiment instead of standard optical light as used in the '808 patent.

The '808 patent states an 'unexpected finding' that simultaneous irradiation of a complex target with a combination of RF energy and light (optical energy) can simultaneously heat both the contrasted and uncontrasted components of complex target to a temperature that destroys both components without raising the surrounding skin temperature to damaging temperatures. Without wishing to be bound by a particular theory, the '808 patent states that simultaneous application of RF and optical energies decreases heat loss from the contrasted portion of a target that occurs with optical radiation alone, and similarly decreases heat loss from the uncontrasted portion of the target when RF energy is used alone.

Like the description in the '808 patent, the third embodiment provides a method and apparatus for dermatological treatment of complicated targets of skin in which RF and optical energy are applied, essentially simultaneously, to the skin to heat a target within the skin. By "essentially simultaneously" is meant that the two forms of energy are applied simultaneously, or are applied in rapid succession to one another such that significant cooling of the target does not occur between the first and second applications of energy. The third embodiment may be used for cosmetic treatment of any complicated target such as hair removal, skin rejuvenation and vascular or pigmented lesions. The device includes an applicator with one or more electrode pairs for generation of RF energy and a light source emitting optical energy. Pulsed RF energy applied by the electrodes is applied to the skin either directly or through conductive substance. The frequency of the RF is preferably at least 300 kHz in order to prevent tissue spasms. The light may have a single wavelength or several wavelengths that are preferably selected to be optimal for the color of the contrasted component of the target, and are typically in the range of 500 to 1200 nm.

As described in the '808 patent, heat generation during the application of the RF and optical energies is higher near the skin surface. In order to make heating uniform within the skin, the surface is preferably cooled during treatment. The surface may be cooled by applying a cooled substance such as ice or ethanol to the skin or by using a thermoelectric cooler. The skin is preferably hydrated in order in enhance the penetration of the cooling into the deep layers of the skin, as is known in the art. When the skin is externally cooled at the surface, the RF and optical energy can heat the target to a depth of up to a few millimeters.

Also, as described in the '808 patent, the RF electrodes may optionally be used to monitor skin impedance during the treatment. Since increasing skin temperature leads to a change in impedance, monitoring the skin impedance allows the temperature distribution in the skin to be followed so that the parameters of the treatment may be altered to optimize the treatment. The temperature distribution in the skin depends on the delay between the cooling and the application of the RF and optical energies, the selection of pulse parameters. The temperature distribution within the skin may thus be controlled by controlling the delay between the time the cooling is applied, and the time the RF and optical energy are applied A microprocessor (running computer program code stored in a computer readable medium, such as a computer disk) may be used for determining the optimal delay time (t) in response to a selected skin temperature profile. This may be calculated as is known in the art, for example, using the equation $t=d^2/(4A)$, where d is the cooling depth, which in this case is about equal to the thickness of the epidermis (0.1 mm), and A is the skin diffusivity (about $1.4\times10^{-3}$ cm$^2$/sec. Alternatively or additionally, the temperature distribution may be controlled by controlling the pulse duration of the RF energy as is known in the art.

Referring now to FIG. 4, a device for applying, essentially simultaneously, RF and quasi-fractional intense pulse light optical energies in accordance with the third embodiment of the invention is shown. An applicator 703, to be described in detail below, contains a pair of RF electrodes and a light source. The light source, which has a shield provided along an optical light path towards a patient's skin, outputs quasi-fractional intense pulse light as described above with respect to the first and second embodiments. The applicator 703 is adapted to be applied to the skin of an individual 705 in the region of a complex target. The applicator 703 is connected to a control unit 701 via a cable 702. The control unit 701 includes a power source 708. The power source 708 is connected to an RF generator 715 that is connected to the RF electrodes in the applicator 703 via wires in the cable 702. The power source 708 is also connected to the light source in the applicator 703 via wires in the cable 702. The control unit 701 contains a refrigeration unit 712 that cools a fluid such as ethanol or water for cooling the applicator 703. The cooled fluid flows from the refrigeration unit 712 to the applicator via a first tube in the cable 702, and flows from the applicator 703 back to the refrigeration unit via a second tube in the cable 702. The control unit 701 has an input device, such as a keypad 710, which allows an operator to input selected values of parameters of the treatment, such as the frequency, pulse duration and intensity of the RF energy or the wavelength and intensity of the optical energy. The control unit 701 optionally contains a processor 709 for monitoring and controlling various functions of the device. For example, the processor 709 may monitor the electrical impedance between the electrodes in the applicator 703, and determine the temperature distribution in the vicinity of the target. The processor 709 may also determine the parameters of the treatment based upon the impedance measurements.

FIG. 5 shows the applicator 703 in detail. The applicator contains a pair of electrodes 401 and 402 that apply RF energy to the skin. A quasi-fractional light source 403 (with a shield, not shown, as described above with respect to the first and second embodiments) produces quasi-fractional light that is delivered to the skin surface by light guide 404. The housing and electrodes are cooled by fluid cooled by the refrigeration unit 712 that flows in a tube 408 between inlet 405 and outlet 406. The inlet 405 and the outlet 406 are connected to the refrigeration unit 712 via the first and second tubes in the cable 702.

Using the system shown in FIG. 4 to apply RF and fractional light optical energies to a target having a diameter of at least 2 mm, the following exemplary parameter values may be used:

Frequency of the RF energy: from about 300 kHz to about 100 MHz.

Output power of the RF energy: from about 5 to about 200 W.

Duration of the irradiation: from about 1 to about 500 msec.

Pulse repetition rate: from about 0.1 to about 10 pulse per second.

Intensity of the quasi-fractional light optical energy: from about 5 to about 100 Joules/cm$^2$.

Pulse duration of the quasi-fractional light optical energy: from about 1 to 200 msec.

While the present invention has been described with respect to the preferred embodiments, other types of configurations may be possible, while remaining within the spirit and scope of the present invention, as exemplified by the claims.

What is claimed is:

1. A system for treating a skin target area comprising:
one or more RF electrodes adapted to provide RF energy for heating the skin target area; and
a quasi-fractional light unit adapted to provide optical spots of energy having a wavelength not greater than 1200 nm for heating the skin target area, the RF electrodes and the quasi-fractional light unit being configured to provide energy essentially simultaneously to the skin target area to heat the entire target in non-uniform manner by way of a matrix of spots each having a predetermined diameter,
wherein the quasi-fractional light unit comprises:
a light source outputting light; and
a shield provided adjacent the light source, the shield including a plurality of holes for creating quasi-fractional light on a side of the shield furthest from the light source, the plurality of holes corresponding to the matrix of spots in a one-to-one relationship,
wherein the shield is made of a ceramic material that allows light to pass therethrough at an attenuated amount, and
wherein the ceramic material corresponds to Aluminum Oxide.

2. The system according to claim 1, wherein the predetermined diameter corresponds to 500 microns, and wherein each spot is spaced apart from adjacently-positioned spots in the matrix of spots by 150 microns.

3. The apparatus according to claim 1, further comprising:
a housing for holding the light source and the shield in place within the apparatus.

4. The apparatus according to claim 1, wherein the light source is a laser light source.

5. The system according to claim 1, the system further comprising a processor,
   wherein the one or more electrodes are configured to measure an impedance of the skin target area, and
   wherein the processor is configured to controlling a delay between heat applied to the skin target area and cooling applied to the skin target area based on the measured impedance.

6. The system according to claim 5, wherein the processor is configured to control a pulse duration of RF energy applied to the skin target area by way of the one or more electrodes, in order to control a temperature distribution of the skin target area.

7. The system according to claim 1, wherein all portions of the shield include Aluminum Oxide.

8. The system according to claim 1, further comprising an optical reflective coating provided on an outer surface of the shield.

9. The system according to claim 8, wherein the optical reflective coating provides for between 70-75% reflectivity of light incident thereon, wherein the shield provides for a 25-30% attenuation of light that pass through non-hole portions of the shield, and wherein the shield provides for no attenuation of light that pass through hole portions of the shield.

* * * * *